(12) United States Patent
Roziere

(10) Patent No.: US 7,570,064 B2
(45) Date of Patent: Aug. 4, 2009

(54) PROXIMITY DETECTOR COMPRISING CAPACITIVE SENSOR

(75) Inventor: Didier Roziere, Nimes (FR)

(73) Assignee: Nanotec Solution, Nimes (FR)

( * ) Notice: Subject to any disclaimer, the term of this patent is extended or adjusted under 35 U.S.C. 154(b) by 0 days.

(21) Appl. No.: 10/526,984

(22) PCT Filed: Sep. 5, 2003

(86) PCT No.: PCT/FR03/02654

§ 371 (c)(1),
(2), (4) Date: Sep. 23, 2005

(87) PCT Pub. No.: WO2004/023067

PCT Pub. Date: Mar. 18, 2004

(65) Prior Publication Data

US 2006/0097734 A1     May 11, 2006

(30) Foreign Application Priority Data

Sep. 6, 2002     (FR) .................................. 02 11089

(51) Int. Cl.
  *G01R 27/26*  (2006.01)
  *A61B 5/103* (2006.01)
  *A61B 5/117* (2006.01)
(52) U.S. Cl. ................. 324/662; 324/658; 600/595; 378/117
(58) Field of Classification Search ............... 324/662; 378/117
  See application file for complete search history.

(56) References Cited

U.S. PATENT DOCUMENTS 3,990,005 A * 11/1976 Abbe et al. ................. 324/662
4,419,713 A    12/1983 Levinson
4,987,583 A *  1/1991 Travanty et al. ............... 378/91
5,065,105 A   11/1991 Bruere et al.
5,315,884 A *  5/1994 Kronberg ................. 73/862.68
5,325,442 A *  6/1994 Knapp ........................ 382/124
5,373,245 A * 12/1994 Vranish ....................... 324/662
5,430,381 A    7/1995 Dower
5,442,347 A    8/1995 Vranish
5,554,973 A    9/1996 Kawashima et al.
5,623,552 A *  4/1997 Lane .......................... 382/124

(Continued)

FOREIGN PATENT DOCUMENTS

FR     2 640 373     6/1990

(Continued)

*Primary Examiner*—Timothy J Dole
*Assistant Examiner*—John Zhu
(74) *Attorney, Agent, or Firm*—Young & Thompson

(57) ABSTRACT

A proximity detector employs a capacitive sensor, having: at least one detection antenna including numerous capacitive proximity sensors which each include a measuring electrode, the antenna being positioned close to an object or body; electronic elements for exciting the electrodes and processing the distance measurement signals originating from the capacitive sensors; and digital elements of controlling the electronic elements and of calculating the distances between the electrodes and the body or object using the processed measurement signals. The detection antenna also contains a single guard for all of the measuring electrodes. Moreover, the electronic elements have, for each detection antenna, a floating or floating excitation capacitive bridge which co-operates with polling elements in order sequentially to measure the respective capacitances between each electrode and the object or body to be measured.

18 Claims, 3 Drawing Sheets

U.S. PATENT DOCUMENTS

| | | | |
|---|---|---|---|
| 5,651,044 A * | 7/1997 | Klotz et al. | 378/117 |
| 5,726,581 A * | 3/1998 | Vranish | 324/688 |
| 5,883,935 A * | 3/1999 | Habraken et al. | 378/117 |
| 5,952,835 A * | 9/1999 | Coveley | 324/671 |
| 5,982,835 A | 11/1999 | Kim et al. | |
| 6,225,939 B1 * | 5/2001 | Lind | 342/4 |
| 6,348,862 B1 * | 2/2002 | McDonnell et al. | 340/562 |
| 6,408,051 B2 * | 6/2002 | Habraken et al. | 378/117 |
| 6,411,727 B1 * | 6/2002 | Harkin | 382/124 |
| 6,661,240 B1 * | 12/2003 | Johnson et al. | 324/662 |
| 6,693,440 B2 * | 2/2004 | Basir et al. | 324/662 |
| 6,703,845 B2 * | 3/2004 | Stanley et al. | 324/663 |
| 2002/0122006 A1 * | 9/2002 | Crawford | 343/702 |

FOREIGN PATENT DOCUMENTS

| | | |
|---|---|---|
| FR | 2 750 648 | 1/1998 |
| FR | 2 756 048 | 5/1998 |
| FR | 2756048 A1 * | 5/1998 |
| WO | WO 97/19638 | 6/1997 |
| WO | WO 97/30633 | 8/1997 |

* cited by examiner

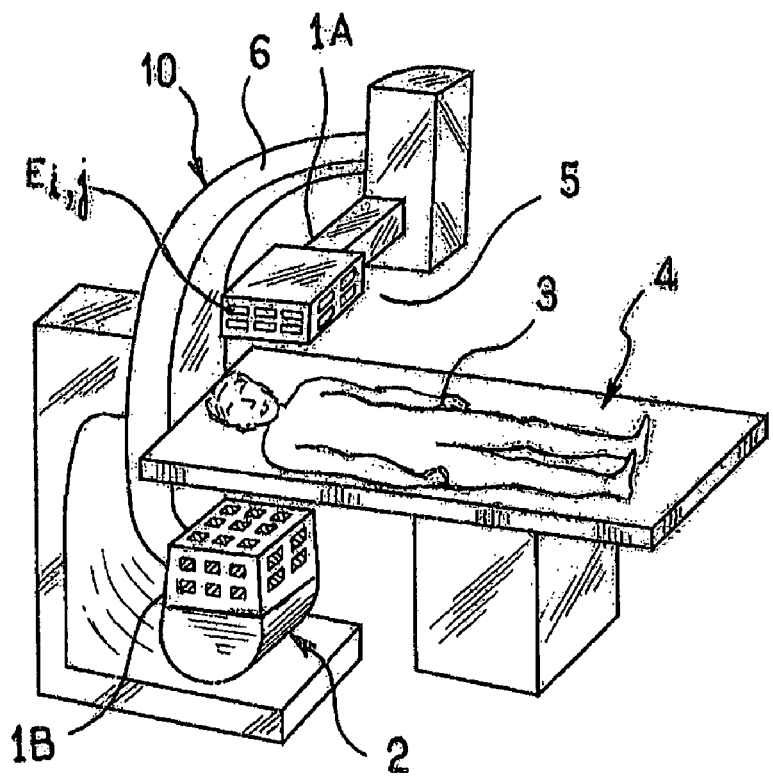
FIG_1
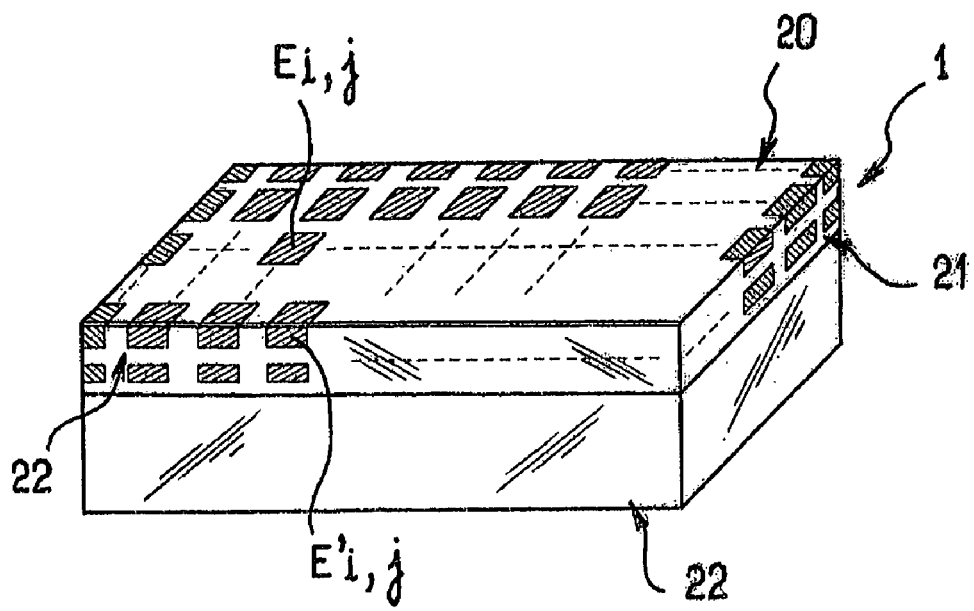
FIG_2

PROXIMITY DETECTOR COMPRISING CAPACITIVE SENSOR

BACKGROUND OF THE INVENTION

The present invention relates to a proximity detector employing a capacitive sensor.

In a numerous industrial applications, the proximity between a machine and an obstacle must be detected and measured, whether this is another object or an individual, in order to deliver proximity distance information, alarm signals and to act as a result.

By way of non-limitative example, the industrial application of this type of detector which can be mentioned is the management of an anti-collision function between mobile or stationary robots and an obstacle, management of an anti-burglary function and, more generally, any management implementing proximity detection.

In the medical field, various robots used for the auscultation of patients need to know the position of the patient relative to the moving parts of the machine.

By way of example, for applications in radiology or in imaging, or also for a medical or surgical treatment, it is essential to be able to provide the operator of a piece of equipment or automated control systems with information which is as exact as possible concerning the position of the patient in order to position the auscultation elements rapidly and correctly.

As regards radiology systems employing X-rays, knowledge in real time to a matter of millimeters of the position of a piece of radiology equipment relative to a patient and its immediate hardware environment would allow the speed of the machine's movements to be increased, enhance safety, and minimise exposure times to X-rays.

To increase the speed of movement of vascular positioners, at the same time as guaranteeing no collision with the patient is one of the current aspirations. However, as the physiognomy of the patient and his position relative to the reference frame of the machine is unknown, the speeds at which these robots move are low in order that the moving parts of the machine do not accidentally injure the patient. Generally, an emergency shutdown comprising mechanical circuit breakers stops all movement when the X-ray detector or emitter comes into contact with the patient or another part of the equipment; however, the kinetics of moving objects and the short travel of the contactors requires low displacement speeds. Increasing the speed of the robot is only possible if a non-contact device detects the patient at a distance, termed the upper threshold, adequate to slow down the movements before coming into contact with the patient. A minimum distance, termed the lower threshold, allows the anti-collision emergency shutdown function to be carried out.

Currently, there is therefore a genuine requirement for non-contact proximity detectors providing accurate distance information which can be used in specific environments such as that of medical imaging. The documents U.S. Pat. No. 4,987,583, WO 9730633 and WO 9719638 disclose proximity detectors suited to this type of application.

The document U.S. Pat. No. 5,982,835 discloses a non-contact proximity detector. The electronics used comprise an all-or-nothing detector functioning with a FET transistor oscillator connected to an unshielded measurement electrode.

The document U.S. Pat. No. 5,442,347 discloses a proximity detector of the capacitive type with controlled double shielding, functioning in phase difference measurement mode, while using RC constants generated with reference resistances. A shield is created by reproducing the sensor signal using a buffer. However, a major theoretical problem becomes apparent in this concept, as the buffer adds a parasitic capacitance to the capacitance to be measured. This parasitic capacitance is much greater than the capacitance to be measured, which leads to measurement errors and significant instabilities.

The document U.S. Pat. No. 5,554,973 discloses an electrostatic detector of the capacitive type, operating in accordance with a switched capacitance operating principle, without a shield.

The document U.S. Pat. No. 6,348,862 discloses a proximity detector which includes a detection electrode and a plurality of control electrodes situated close to a spatial region in which an object to be detected is sited.

SUMMARY OF THE INVENTION

A principal objective of the present invention is to propose a proximity detector employing a capacitive sensor which provides accurate measurement (typically to the nearest millimeter) of the position of an object at a measured range (typically to an accuracy of some 10 centimeters) greater than that permitted by proximity detectors of the prior art, in particular having the effect of increasing the speed of movement of radiology machines and providing a topography of the patient with the aim of evaluating his thickness in order to optimise the power at which the X-rays are transmitted and thus minimise the level of radiation necessary to produce an image.

This objective is achieved with a capacitive proximity detector comprising:
- at least one detection antenna comprising a plurality of capacitive proximity sensors, each incorporating a measurement electrode, said antenna being placed close to an object or a body,
- electronic means for exciting said measurement electrodes and for processing the signals originating from said capacitive sensors,
- digital means for controlling the electronic means and for calculating from the measurement signals thus processed, the distances between said electrodes and said object or said body.

According to the invention, the electronic means comprise, for each detection antenna, a floating capacitive bridge, or a capacitive bridge with floating excitation, cooperating with polling means to measure sequentially the respective capacitances between each electrode of said antenna and the object or body to be measured.

This allows the production of a pixel camera equivalent in which each pixel is constituted by an electrode. This camera, when moved along a patient's body, will allow the production of a topography of this patient in order to obtain a measurement of his body thickness.

The floating capacitive bridge should be of the type disclosed in the document FR 2756048. A capacitive measurement chain of the type described in the document FR 2640373, which employs a polarisation voltage source and a triaxial transformer, can also be used.

The proximity detector according to the invention, constituted by a plurality of measurement electrodes, orientated along several axes so as to cover all relevant areas, can be produced as several detection antennas.

In one preferred form for producing a proximity detector according to the invention, the detection antenna also comprises a single shield for all the measurement electrodes of the antenna.

However, a configuration in which the detection antenna also comprises several shields, each one provided for part of the assembly of antenna measurement electrodes can be envisaged.

The detection antennas can be produced using a rigid or flexible circuit and connected to the electronic means.

The electronic means and the digital control and calculation means can co-operate to measure a distance successively on each antenna electrode, following a predetermined but changeable order.

The detection antennas preferably comprise a test track placed to the rear of or close to the electrodes (flat side of shield), which, in normal operation, is at the potential of the shield and, in test mode, is earthed.

Under these conditions, each electrode sees a parasitic capacitance simulating the presence of an object, in order to verify the integrity of the proximity detector.

The electronic means and the digital control and calculation means cooperate to deliver an alarm signal indicating an inconsistent measurement or a malfunction of the digital control and calculation means.

It can also be envisaged that the electronic means comprise one or more reference capacitances for checking the calibration of the electronics or carrying out an automatic recalibration.

In one particular configuration of a proximity detector according to the invention, shielding or earthing surfaces arranged to modify the field lines of the electrodes, can be placed close to said electrodes. Thus, specific surface area forms equivalent to said measurement electrodes can be created.

In one particular embodiment, the proximity detector according to the invention is arranged on the inside or outside surface of a cap or box housing, for example, the X-ray imaging detector or the X-ray emitter.

The electronic means and the digital control and calculation means cooperate to deliver proximity detection threshold alarm signals. The distances measured between the electrodes and the objects detected are delivered in digital and analogue form.

To provide for movements following the six degrees of freedom, the antennas are, for example, placed on five faces of the box or cap.

If this is a proximity detector used in a radiology system using X-rays, comprising a device to emit an X-ray beam intended to irradiate an object or a body, an antenna, termed X-ray antenna, is then crossed at least partially by the X-ray beam.

In one simple configuration, the X-ray antenna can for example comprise a piercing to allow the X-ray beam to pass through. This area is then non-measuring, as it is not provided with electrodes.

To overcome this disadvantage, it is then possible to make provision that the X-ray antenna be, in the area of the X-ray beam, produced from materials that are at least partially transparent to X-rays. This production is possible using a flexible printed circuit composed of an insulator metallised on its two sides with a very thin layer of chromium forming the base layer for a layer of copper, said copper layer being removed by chemical attack over the area which corresponds to the passage of the X-ray beam in order to leave on the insulator only the thin layer of chromium in which the linking tracks, the capacitive electrodes, the test track and the shield are produced (FIG. 5). The X-ray emitter can also be provided with so-called X-ray antennas.

This last configuration allows complete coverage of the electrodes of the detector in order to increase the efficiency of this detector.

The proximity detector according to the invention is distinguished in particular from the detector disclosed in the document U.S. Pat. No. 5,952,835 by the fact that, in the present invention, the electronics function by amplitude measurement with a shield, and that the oscillator has constant characteristics independent of the capacitance to be measured. Moreover, the detector according to the invention operates by measuring amplitude and not by measuring phase difference.

This proximity detector device allows an increase in the speed of displacement of current radiology machines, safety detection (anti-collision), the production of a rough image in three dimensions of the patient, the evaluation of the thickness of a patient in order to optimise the power of the X-rays to produce images with the minimum of radiation, and to improve image quality.

The proximity capacitive detector according to the invention allows control of the approach of a vascular positioner for medical application, using several antennas, equipped with a multitude of capacitive electrodes, housed in the detector. Said device measures in real time several absolute distances (one distance per electrode) separating the surface of the detector cap and the surrounding objects such as a patient or the table.

Proximity detector devices according to the invention can also be used in moving machines or robots, in particular machine tools, industrial robots, transport vehicles, etc.— with the effect of increasing their speed of operation and improving safety.

BRIEF DESCRIPTION OF THE DRAWINGS

Other advantages and characteristics of the invention will become apparent on examination of the detailed description of a method of implementation, which is in no way limitative, and the attached drawings, in which:

FIG. 1 is a block diagram of a piece of radiology equipment incorporating two proximity detectors according to the invention;

FIG. 2 illustrates the layout of an antenna in a proximity detector according to the invention;

DESCRIPTION OF THE PREFERRED EMBODIMENTS

Figure 3:
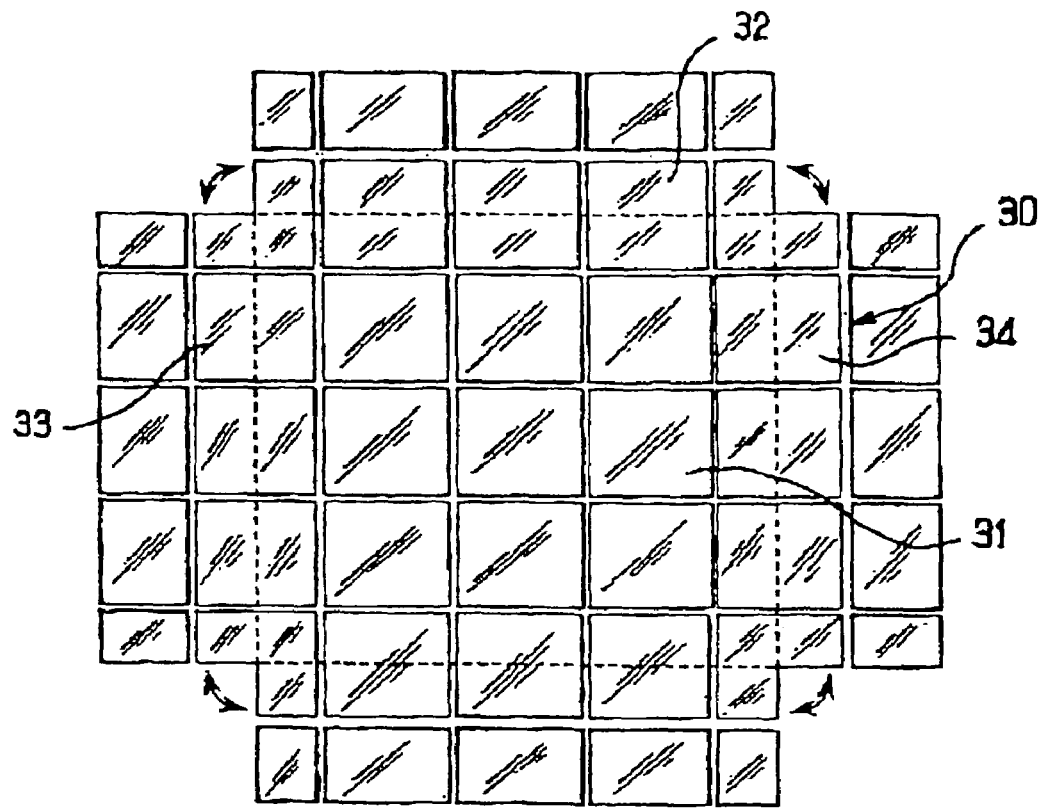
FIG. 3 illustrates an example of the structure of an antenna of a proximity detector according to the invention.

There will now be described, with reference to FIG. 1, an embodiment of proximity detectors according to the invention in an X-ray radiology machine for a vascular positioner.

A first proximity detector (1A) is arranged inside an X-ray detector device (5) fitted to a radiology machine (10), and comprising several antennas lining five of the internal or external walls of the cap of the X-ray detector, each antenna comprising a plurality of electrodes $E_{i,j}$. A second proximity detector (1B) is arranged on the inside surface of the X-ray emitter device of the machine (10). The X-ray emitter device (2) and the X-ray detector device (5) are installed at the two ends of a C-shaped moving part rotating around an examination table (4) on which a patient (3) is lying.

By reference to FIG. 2, a proximity detector according to the invention 1 comprises an antenna 20 arranged on the inside surface of the cap 22 and the side faces 21, 22. The antenna 20 is constituted by a plurality of electrodes arranged as a matrix, comprising electrodes $E_{i,j}$ situated in full on one face, electrodes $E'_{i,j}$ arranged on edge on two faces, and electrodes all arranged on the sides.

It should be noted that the antenna 20 could also be arranged on the outside surface of the detector cap.

There will now be described, with reference to FIG. 3, an embodiment of an antenna 30 in the form of a flexible circuit. This antenna 30 lines the inside surface of a main face of a cap with electrodes 31 and the inside surfaces of the side faces of the cap with electrodes 32, 33, 34. These electrodes are all connected to a board via linking tracks 40, shown on FIG. 6.

Figure 5:
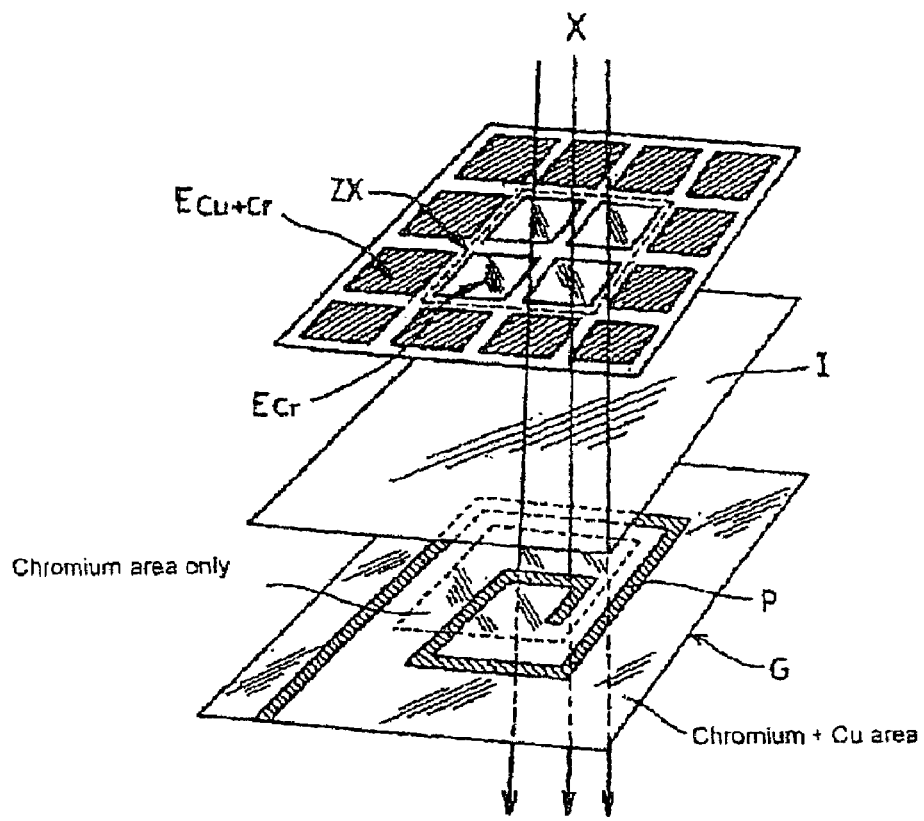
FIG. 5 illustrates the structure of a flexible circuit used to produce an antenna in a proximity detector.

The antennas fitted to proximity detectors according to the invention can be produced using a multi-layer technique, as illustrated diagrammatically in FIG. 5. To produce the so-called X-ray antenna, a flexible printed circuit 60 composed of an insulator I metallised on its two faces with a thin layer of chromium Cr and a thick layer of copper Cu, the two copper layers being removed over an area ZX which corresponds to the passage of the X-ray beam and in which the linking tracks, the capacitive electrodes $E_{cr}$, a test track P, and a shield are produced from the two layers of chromium.

A conducting shield layer G in copper+chromium, the electrodes $E_{Cu+Cr}$ in copper+chromium, and the electrodes $E_{Cr}$ in chromium are produced according to an industrial process using multi-layer flexible circuits of "adhesiveless" type having, on a polyimide support, a thin layer of chromium covered with copper. This industrial process is controlled by the manufacturers of flexible circuit.

Figure 4:
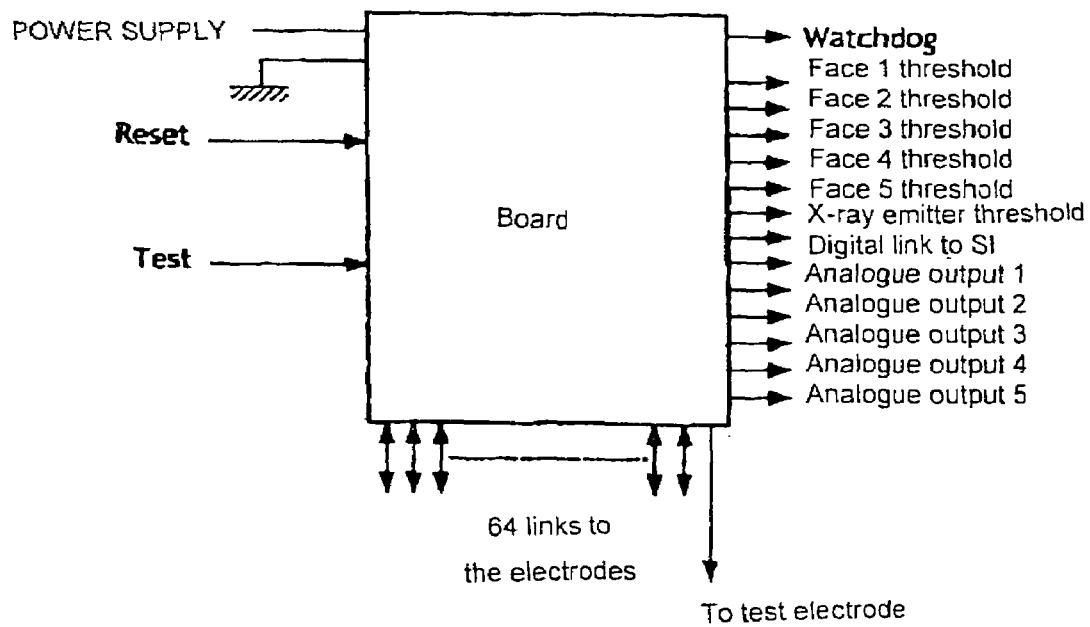
FIG. 4 represents diagrammatically the inputs to and outputs from a board fitted to a proximity detector according to the invention.

A board used in a proximity detector according to the invention comprises, with reference to FIG. 4, 64 links to the electrodes of three detection antennas, a test input connected to a test electrode for each antenna, a Reset input for reinitialising, and a DC supply input.

This board accepts a "Watchdog" alarm signal, five alarm threshold detection signals (objects or patients too close), an X-ray emitter detection signal, five analogue output signals corresponding to the five faces of the cap, an analogue output signal detecting the X-ray emitter, a test electrode excitation signal, and a serial digital signal to communicate with the central processing unit of the equipment.

The "Watchdog" alarm signal is placed at low level in case of inconsistent measurements, no electrode or software failure. The analogue outputs are images of the minimum distances from the face of the detector, from the sides of the detector, or from the emitter. The Reset signal is a signal to reinitialise the micro-controller. The digital link provides the 64 distances measured and that the proximity detector is operating correctly. The sensor is directly connected to the central processing unit SI of the equipment without an interface card.

Figure 6:
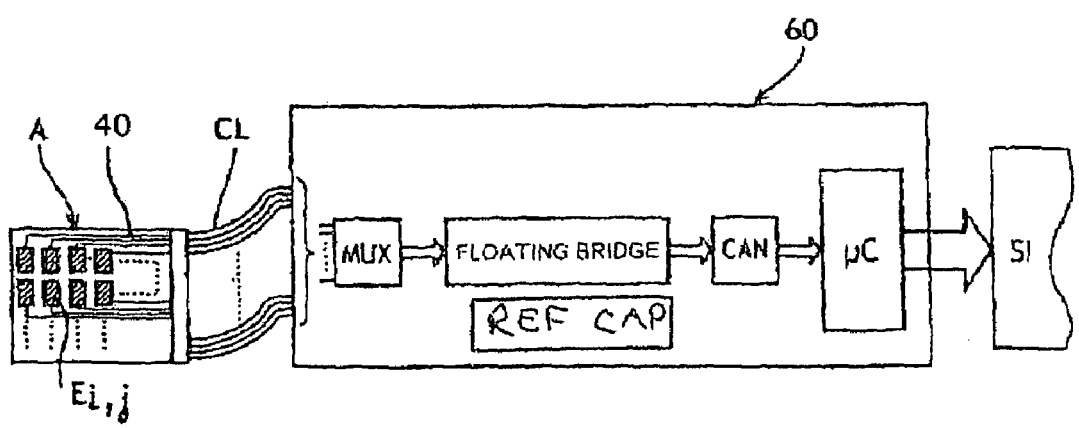
FIG. 6 illustrates the structure of a measurement chain forming part of a proximity detector according to the invention.

As shown in FIG. 6, an antenna A of a proximity detector according to the invention is connected via a flexible connecting cable CL to a board 60, including an analogue multiplexer enabling polling of the input, a multi-channel capacitive floating bridge using a technology disclosed in the document FR2750648, corresponding to French patent no. 96 13992 of 15$^{th}$ Nov. 1996, an analogue/digital conversion module, and a digital module for calculating distances, checking satisfactory operation and communication with the information system SI and controlling the machine.

There will now be described the operation of a proximity detector according to the invention, with reference to the aforementioned figures. The proximity detector measures a distance successively on each electrode following an order which can be changed simply in the software.

The proximity detector has a test electrode which, in normal operation, is at the shield potential and which, when it is earthed, is used to test correct operation of the sensor and the serviceability of the assembly connection+antenna.

By implementing the test command, it will also test the measurement chain of each sensor for correct operation.

If a distance measured on one of the electrodes reaches a predefined low threshold, the software output which corresponds to the antenna which supports the electrode moves to the low state, and it will revert to the high state when the distance again exceeds the threshold. The "Watchdog" alarm output moves to the low state if any one of n measurements is inconsistent (test failure) or if the micro-controller is blocked or defective.

Initially, the digital outputs are the images of the distances measured for each electrode, but the processing can then become more complex, and therefore the micro-controller (or DSP) should be provided with reserve calculating power.

There will now be described a practical example of the manufacture of a proximity detector according to the invention.

In this practical example, the electrical module is arranged on a board 160 mm in length and 100 to 160 mm in width, and comprises a connector for the analogue outputs (twisted and shielded), a connector for the software inputs/outputs, a power supply connector, and several connectors for the electrode signals.

The antennas which occupy the edges of the detector will have half of their surface on the side and the other on the large face. There are 33 electrodes distributed over the 4 antennas; 3 antennas for the detector and one antenna for the X-ray emitter. 13 electrodes are situated on the antennas on the side of the detector, 16 on the X-ray antenna and 2 on the X-ray emitter.

The range of the sensors is greater than 100 mm with a resolution of the order of millimeters, which allows control of the speed at which the detector approaches the patient to be optimised (maximum speed with minimum risk of impact).

The cables which connect the electronics to the antennas of the side of the X-ray emitter are subject to movement and must in practice accommodate a dynamic radius of curvature of 50 mm.

To allow replacement of the antenna of the side of the X-ray emitter or the electronics without removing the cable, the latter is, for example, fitted with a connector on the antenna side and with a connector on the electronics side. It is also possible to provide a shield strap on the sides of the detector in order to modify the field lines of the electrodes so as to modify the equivalent surface areas of these electrodes and their measurement span and their range.

As this is a safety device, the detection distance must be very reliable and the system must be capable of being warned in the event of failure. Under real conditions, the surroundings to the equipment are very congested. The objects to be detected are of different types; a human body (patient lying on the mattress on the table or a doctor standing at the side of the table), metallic parts which may or may not be earthed, and non-metallic parts which are slightly conducting. Detection must work in any direction. Detection takes place over the whole of the active surface of the detector and on its edges, which corresponds to five of the sides of a box.

The X-ray antenna must be quasi-transparent to X-rays, which implies the use of metal which is not very thick for the production of the electrodes and the shield. Doctors generally install light plastic protection on the detector (Charlotte). The order of magnitude of the time in which a complete proximity must be detected is 50 ms for an antenna with 64 electrodes. The size of the objects to be detected is variable: from the patient's abdomen to his hand, a finger or his nose.

Of course, the invention is not limited to the examples which have just been described and numerous arrangements can be made to these examples without departing from the scope of the invention. More generally, proximity detectors according to the invention can be used in any industrial application, which this involves detecting complex shapes or a presence using multi-electrode antennas. Thus, proximity detectors according to the invention can be provided for mobile robots or transport vehicles, to improve safety around these equipments. Proximity detectors according to the invention can also be used in anti-burglary devices and in anti-collision devices.

The invention claimed is:

1. Proximity detector employing a capacitive sensor, comprising:
   at least one detection antenna comprising a plurality of capacitive proximity sensors that each includes only a single measurement electrode, said antenna movably approaching an object or a body,
   electronic means for exciting said measurement electrodes and for processing the signals originating from said capacitive sensors,
   digital means for controlling the electronic means and for calculating in real time, from the measurement signals thus processed, the absolute distances between said electrodes and said object or said body,
   wherein said electronic means comprise, for each said detection antenna, a floating capacitive bridge or with floating excitation, cooperating with polling means to measure sequentially the respective capacitances between each of said measurement electrodes of said antenna and the object or body to be measured, and
   wherein said sensors have a range greater than 100 mm with a resolution of the order of a millimeter.

2. Proximity detector according to claim 1, characterised in that the detection antenna also comprises at least one shield for all the measurement electrodes of the antenna.

3. Proximity detector according to claim 1, characterised in that the electronic means and the digital control and calculation means cooperate to measure a distance successively on each electrode of an antenna according to a predetermined but changeable order.

4. Proximity detector according to claim 1, characterised in that the electronic means and the digital control and calculation means cooperate to deliver an alarm signal indicating an inconsistent measurement or a malfunction of the digital control and calculation means.

5. Proximity detector according to claim 1, characterised in that the electronic means also comprise one or more reference capacitances provided to check the calibration of said electronic means or to recalibrate said electronic means.

6. Proximity detector according to claim 1, characterised in that one antenna also comprises, close to the measurement electrodes, one or more shield or earthing surfaces which are arranged to modify the field lines of the measurement electrodes.

7. Proximity detector according to claim 1, wherein the proximity detector is arranged on the inside or outside surface of a cap or box and comprises a plurality of measurement areas equipped with detection antennas.

8. Proximity detector according to claim 7, characterised in that the electronic means and the digital control and calculation means cooperate to deliver analogue output signals of the objects detected.

9. Proximity detector according to claim 7, characterised in that the antennas are arranged on five faces of the box or cap.

10. Proximity detector according to claim 7, wherein the proximity detector comprises edge antennas arranged in part over one face of said cap, and in part over another contiguous face, and lateral antennas.

11. Proximity detector according to claim 1, characterised in that the electronic means and the digital control and calculation means cooperate to deliver proximity detection threshold signals.

12. Proximity detector according to claim 1, characterised in that at least one of the antennas is produced using a flexible circuit.

13. Proximity detector according to claim 1, characterised in that at least one of the antennas is connected to the electronic means by flexible connecting means.

14. Proximity detector according to claim 1, used in a piece of radiology equipment employing X-rays, comprising a device for emitting an X-ray beam intended to irradiate an object or a body and a device for detecting the X-rays originating from said object or body, this X-ray detector device being covered by a cap, wherein the proximity detector is arranged on the inside or outside surface of said cap.

15. Proximity detector according to claim 1, fitted in a piece of radiology equipment employing X-rays, comprising a device for emitting an X-ray beam intended to irradiate an object or a body, wherein the detector is arranged on the inside or outside surface of said emitter device.

16. Proximity detector employing a capacitive sensor, comprising:
    at least one detection antenna comprising a plurality of capacitive proximity sensors, each comprising a measurement electrode and a shield, said antenna being placed close to an object or a body;
    electronic means for exciting said measurement electrodes and for processing the signals originating from said capacitive sensors;
    digital means for controlling the electronic means and for calculating, from the measurement signals thus processed, the distances between said electrodes and said object or said body;
    said electronic means comprising, for each detection antenna, a floating capacitive bridge or with floating excitation, cooperating with polling means to measure sequentially the respective capacitances between each electrode of said antenna and the object or body to be measured,
    wherein at least one of the detection antennas comprises a test track which, in normal operation, is at the potential of the shield and, in test mode, is earthed.

17. Proximity detector according to claim 16, characterised in that the test track is placed to the rear of or close to the electrodes.

18. Proximity detector employing a capacitive sensor, comprising:
    at least one detection antenna comprising a plurality of capacitive proximity sensors, each comprising a measurement electrode, said antenna being placed close to an object or body to be measured;

electronic means for exciting said measurement electrodes and for processing signals originating from said capacitive sensors;

digital means for controlling said electronic means and for calculating, from measurement signals thus processed, distances between said electrodes and the object or body;

wherein said electronic means comprise, for each detection antenna, a floating capacitive bridge or with floating excitation, cooperating with polling means to measure sequentially the respective capacitances between each said electrode of said antenna and the object or body wherein the proximity detector is used in a piece of radiology equipment employing X-rays and comprising a device for emitting an X-ray beam intended to irradiate the object or body and a device for detecting the X-rays originating from the object or body, said detector device being covered by a cap, the proximity detector being arranged on the inside or outside surface of said cap, wherein said detection antenna comprises a flexible printed circuit composed of an insulator metallised on both faces with a thin layer of chromium then by a layer of copper, said copper layer being removed over an area which corresponds to a passage for the X-ray beam and in which linking tracks and the capacitive proximity sensors are produced from the chromium layer.

* * * * *